(12) United States Patent
James et al.

(10) Patent No.: US 8,466,285 B2
(45) Date of Patent: Jun. 18, 2013

(54) USE OF GRINDING IN CHEMICAL SYNTHESIS

(75) Inventors: Stuart Lloyd James, Belfast (GB); Ana Lazuen-Garay, Belfast (GB); Anne Pichon, Belfast (GB)

(73) Assignee: The Queen's University of Belfast, Belfast (GB)

( * ) Notice: Subject to any disclaimer, the term of this patent is extended or adjusted under 35 U.S.C. 154(b) by 1436 days.

(21) Appl. No.: 11/990,962

(22) PCT Filed: Aug. 25, 2006

(86) PCT No.: PCT/GB2006/003180
§ 371 (c)(1), (2), (4) Date: Mar. 13, 2008

(87) PCT Pub. No.: WO2007/023295
PCT Pub. Date: Mar. 1, 2007

(65) Prior Publication Data
US 2009/0143595 A1 Jun. 4, 2009

(30) Foreign Application Priority Data
Aug. 25, 2005 (GB) .................................. 0517414.9

(51) Int. Cl.
C07F 1/08 (2006.01)
B01J 31/12 (2006.01)

(52) U.S. Cl.
USPC .................. 546/2; 502/151; 562/480

(58) Field of Classification Search
USPC .................. 502/151; 562/480; 546/2
See application file for complete search history.

(56) References Cited

U.S. PATENT DOCUMENTS
6,491,740 B1   12/2002   Wang et al. ........................ 95/90

FOREIGN PATENT DOCUMENTS
| EP | 1070538 A2 | 1/2001 |
| WO | 2005/071704 A2 | 8/2005 |
| WO | 2007/023295 A3 | 3/2007 |

OTHER PUBLICATIONS

Chapman, M.E. et al., "Synthesis, X-ray Structures, and Magnetic Properties of Copper (II) Pyridinecarboxylate Coordination Networks," *Crystal Growth & Design*, vol. 1(2), pp. 159-163, 2001.

Chul, S.S.Y., et al., "A Chemically Functionalizable Nanoporous Material $[Cu_3(TMA)_2(H_2O)_3]$," *Science*, vol. 283, pp. 1148-1150, 1999.

Pichon, A. et al., "Solvent-free Synthesis of a Microporous Metal-organic Framework," *CrystEngComm*, vol. 8, pp. 211-214, 2006.

*Primary Examiner* — Charanjit Aulakh
(74) *Attorney, Agent, or Firm* — Drinker Biddle & Reath LLP

(57) ABSTRACT

A process for the preparation of a multi-dimensional microporous metal-organic compound comprising the steps of providing a first reactant which includes at least one metal in ionic form, providing a second reactant which includes a bridging organic ligand, grinding the first and second reactants together, wholly or substantially in the absence of solvent.

16 Claims, 6 Drawing Sheets

USE OF GRINDING IN CHEMICAL SYNTHESIS

The present invention relates to a process for the preparation of microporous two- and three-dimensional metal-organic compounds.

Microporous two- and three-dimensional compounds are compounds or materials which have a multi-dimensional structure comprising channels or open cavities, usually of a crystalline nature. These structures, or frameworks, with pores or channels can have a wide range of technological applications, for example as storage for hydrogen gas, or as zeolites.

Zeolites are some of the most well known of these compounds. They can have a hydrous framework of aluminosilicates or their derivatives and have relatively large channels. They are used as molecular sieves, desiccants, adsorbent, ion exchangers, and catalysts. However, many existing zeolites are not easy to manipulate at the molecular level, such that there has been an increasing trend towards other microporous materials based on building blocks other than silicon, aluminium and oxygen, specifically metal ions and organic groups.

Such microporous metal-organic compounds offer great potential for chemical and structural diversity. Compounds like $Cu_3(BTC_2)$ (usually abbreviated to "Cu-BTC"), wherein BTC=benzene-1,3,5-tricarboxylate, is a highly porous metal-organic coordination polymer. This material creates a 3-dimensional system of channels with a pore size of about 1 nm, and an accessible porosity of about 40% in the solid form. Unlike zeolites, the channel linings can be chemically functionalised—for example, the water ligands can be replaced by pyridines (Science—Chui et al.283.5405:1148).

The preparation of Cu-BTC is generally carried out by the mixing and heating of copper nitrate trihydrate and benzenetricarboxylic acid (also termed trimesic acid) in a solvent according to the following equation:

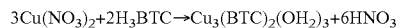

However, the known syntheses of Cu-BTC have two major drawbacks; time and yield. The Science reference above mentioned describes how the components are mixed and heated at 180° C. for twelve hours in a Teflon-lined pressure vessel, resulting in a 60% yield along with copper metal and copper oxide, which must be separated out. An alternative method is mentioned as Example 1 in U.S. Pat. No. 6,491,740, wherein the components are mixed for thirty minutes, poured into an autoclave, and then heated at 110° C. under hydrothermal conditions for seventeen hours.

The same drawbacks arise for the synthesis of another known microporous three dimensional material, copper isonicotinate: $[Cu(INA)_2]$. Currently, the compound is obtained from isonicotinic acid and copper nitrate by heating for five days in a mixture of ethanol, acetonitrile and water (Chem. Commun. 2002, 1340, Lu et al.).

It is not considered that such processes are effective for the quantitative synthesis of 2D or 3D metal-organic compounds which can support open cavities. As described above, such microporous metal-organic compounds are usually obtained using a solvent and heat. The yield obtained using these "solvothermal" methods is reasonable for laboratory use, but they are inefficient on an industrial scale in terms of time, separation of additional material (e.g. solvents), and heating.

One object of the present invention is to provide a simpler synthesis for providing multi-dimensional metal-organic compounds, which is also capable of providing an economical yield, and with increased efficiency in terms of materials, time, cost or energy, compared to the "solvothermal" methods, whilst also being environmentally friendly.

Thus, according to one aspect of the present invention, there is provided a process for the preparation of a multi-dimensional microporous metal-organic compound, wherein a first reactant which includes at least one metal in ionic form, and a second reactant which includes a bridging organic ligand, are ground together wholly or substantially in the absence of solvent, optionally at ambient temperature.

Preferably, the metallo-organic compound formed has permanent porosity.

The process of the present invention has been found to work at room or ambient temperature, or indeed the temperature created by the grinding. Heating could be applied to the process if desired or necessary.

A liquid, optionally one or more liquids, which may or may not act as a solvent, is generally not required but can optionally be added.

Such a liquid may be any substance, including organic solvents and water. Such a liquid may act as a lubricant more than a solvent, but still have some solvating ability. Hence, the process of the present invention is wholly or substantially in the absence of solvent, as any liquid added may unintentionally also be a solvent. A low or very low volume of a liquid (in proportion to the reactants, for example <10% wt, or even <5% or <3% or even <1%), can therefore still be involved, but as an additive to assist the process which is proceeding due to the grinding action.

It is also noted that one or more by-products of the process of the present invention may be a solvent or solvents, e.g. water or an organic acid such as acetic acid. Such by-products are not intended to be part of the process of the present invention.

The grinding is generally provided by the use of one or more grinders or grinding means, which means may include one or more means or grinding assistants to assist grinding, or at least to assist the admixture of the reactants. Such means includes a grinder or mill, optionally including one or more grinding balls such as (steel) ball bearings. Alternatively, other grinding methods could be considered. The time and method of grinding can be adapted to the nature of the reactants used or the scale of production desired, but is generally in terms of minutes.

The first reactant may be a salt, or in salt form, such as a nitrate, sulfate, acetate or the like. Such could include divalent first-row transition metal salts $MX_2$ such as M=Cu, $X_2$= $(Oac)_2$, $(HCO_3)_2$, $(F_3CCO_2)_2$, $(acac)_2$, $(F_6acac)_2$, $(NO_3)_2$, $SO_4$; M=Ni, $X_2=(Oac)_2$, $(NO_3)_2$, $SO_4$; M=Zn, $X_2=(Oac)_2$, $(NO_3)_2$. For example, the formation of $[Cu(INA)_2]$ can use copper acetate as a starting material.

Other metals useable in the present invention include sodium and transition metals such as rhodium, zinc, manganese, as well as others mentioned in the Science article referred to above.

The second reactant can be any one of a large number of known organic ligands. However, organic ligands which comprise a bridging atom having at least one non-binding doublet (i.e. a free pair of electrons) available, like oxygen, nitrogen, phosphorus or sulphur, are preferred. For example, the formation of $[Cu(INA)_2]$ can use isonicotinic acid as a starting material, in which the atoms which connect to the copper are one of the oxygen atoms of the carboxylic moiety and the nitrogen of the pyridine moiety.

Suitable ligands include carboxylates, pyridines, amines, carboxylic acids and/or diacids moieties. Examples include 1,4-benzenedicarboxylic acid ($H_2BDC$), acetylenedicarboxylic acid (ADC), 1,3,5-benzenetricarboxylic acid ($H_3BTC$), isonicotinic acid (HINA) and 4,4'-bipyridyl (4,4'-BIPY).

In bulk physical form the compounds formed by the present invention were found to vary from dry free-flowing powders to thick pastes, the latter becoming free-flowing powders on standing in air, and the compounds could be found to be crystalline on examination by XRPD. In many cases the compound can be identified by comparison with single-crystal X-ray data from the Cambridge Crystallographic Database (CSD).

In one embodiment of the present invention, the grinding step is followed by a drying step. Such step can be carried out by simple air drying and/or heating. This step permits to remove any unwanted side products or water from the formed compound of the invention.

In another embodiment of the present invention, the grinding of the first reactant and the second reactant is only partial and/or not continuous for the reaction time required for the process to proceed. In particular, grinding may only be required to initiate the reaction, in particular to divide and mix the reactants.

In another embodiment, more than two reactants can be used to obtain a multi-metal and/or multi-bridging-substance 2D or 3D microporous metal-organic compound.

Thus, the present invention can form materials which contain more than one type of ligand. These include, but are not limited to, pillared-layer structures in which one ligand serves to form a grid-like layer structure with the metal ions, and the second type of ligand acts as a pillar between the layers. In particular, reaction between fumaric acid, 4,4'-bipyridine and zinc(II) acetate gives such a structure $[Zn_2(fumarate)_2(4,4'-bipyridine)]$ in quantitative yield as shown by XRPD.

It is also possible to form interpenetrated structures by the process of the present invention, i.e. structures which consist of more than one network and are structurally interlocked, but which are not chemically bonded to each other. The pillared layer structure described above in an example of this.

The above examples of $Cu_3(BTC)_2$ and $[Zn_2(fumarate)_2(4,4'-bipyridine)]$ also show that it is possible to form framework materials based on SBUs (secondary building units). In these examples the SBU is the dinuclear tetracarboxylate motif, sometimes referred to as a paddle wheel. However other SBUs such as the oxo-centred tetranuclear units $M_4O$ (M=Zn, Be) may also form under such conditions.

It is also possible to form 'inclusion' or 'host-guest' materials by the process of the present invention. For example, reaction between nickel(II)nitrate, 4,4-bipyridine and pyrene gives the framework structure $[Ni(4,4'-bipyridine)(NO_3)_2]$.

It is also possible to form framework materials whose structures are directed by additional templating agents, of which the nickel compound above is an example (in which the framework structure only forms in the presence of pyrene).

Preferably the process of the invention provides quantitative yields of the desired microporous compound.

The present invention extends to multi-dimensional microporous metal-organic compounds whenever formed by the present invention. These include $[Cu(INA)_2]$ and Cu-BTC.

Embodiments of the present invention will now be described by way of example only, with reference to the accompanying figures.

EXAMPLE 1

Synthesis of $[Cu(INA)_2]$

The reagents were purchased from Aldrich and used as supplied.

Synthesis of 1: A 20 cm$^3$ steel vessel was charged with $Cu(OAc)_2.H_2O$ (0.203 g, 1.0 mmol), (although copper formate $Cu(HCO_2)_2.xH_2O$ is a similarly effective starting material for the synthesis), isonicotinic acid (0.252 g, 2.0 mmol) and a steel ball bearing, and shaken with a Retsch MM200 mixer mill (a ball mill grinder) for 10 minutes at an oscillation rate of 25 Hz. No solvent was added.

Figure 1:
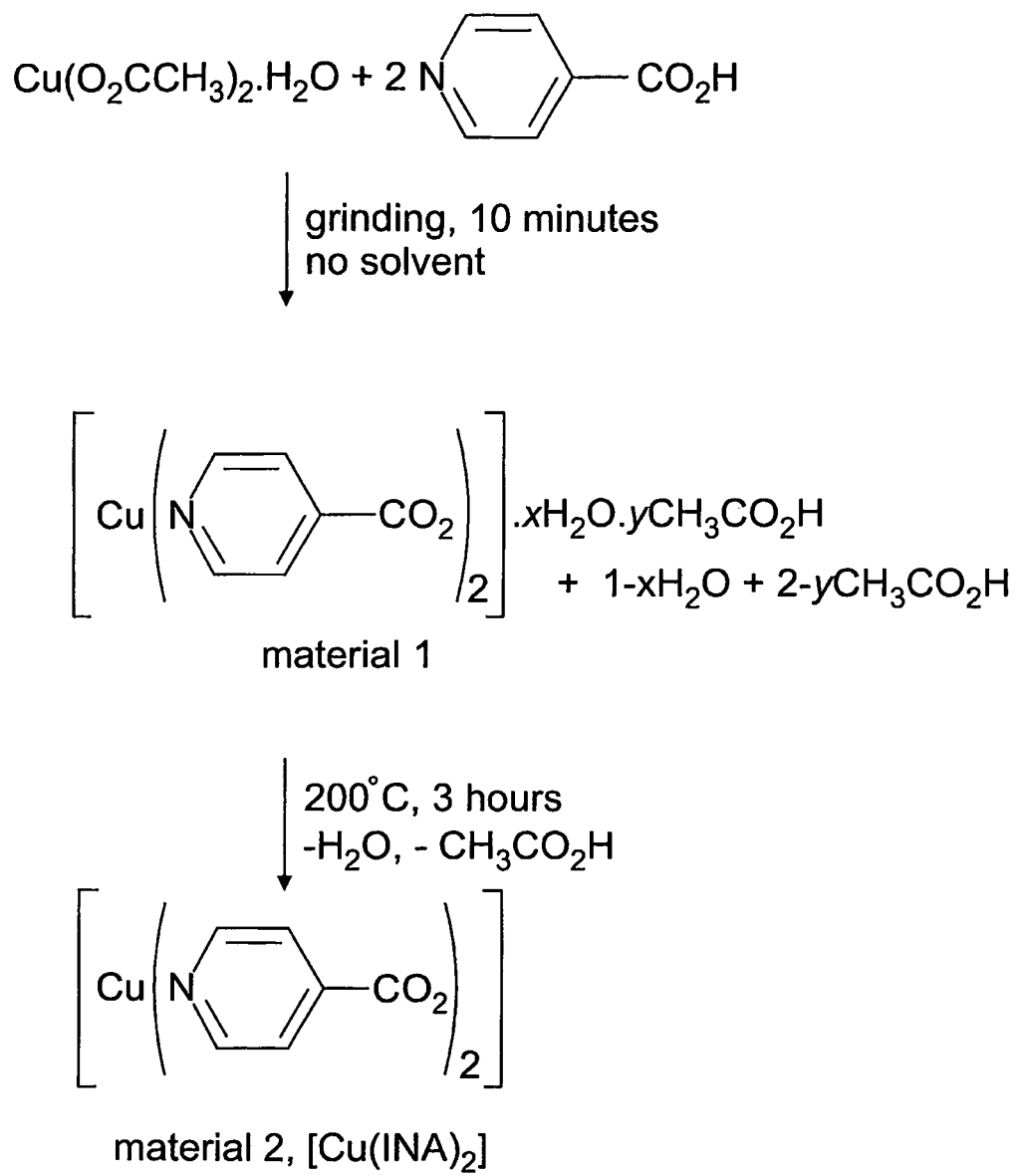
FIG. 1: Solventless reaction scheme between $Cu(OAc)_2.2H_2O$ and isonicotinic acid (INAH) to give the 3D microporous compound $[Cu(INA)_2]$ as product material 1 (with water and acetate ligands), and as product material 2 once dried.

A reaction was observed between copper acetate monohydrate, $Cu(O_2CCH_3)_2.H_2O$, and isonicotinic acid, $NC_5H_4$-4-$CO_2H$ (INAH), to give a new material, labelled "material 1" in FIG. 1, as indicated by a change in colour from green to blue and the characteristic odour of acetic acid, released as a by-product (FIG. 1). X-ray powder diffraction showed the product to be highly crystalline, and indicated that the reaction was quantitative.

Figure 2A:
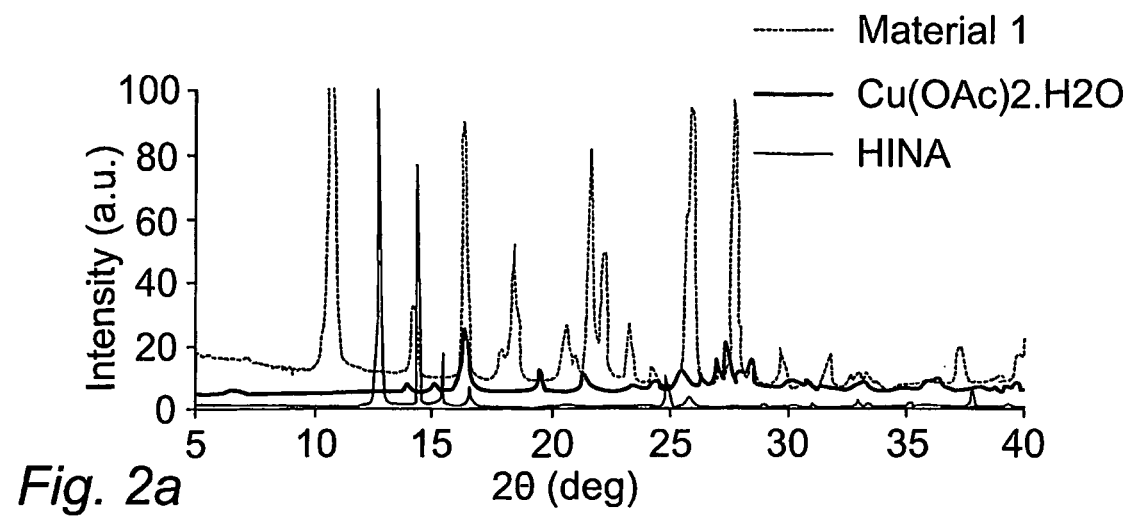
FIG. 2a: Comparison of XRPD patterns of starting materials $Cu(OAc)_2.H_2O$, isonicotinic acid (HINA), and the product material 1.
Figure 2B:
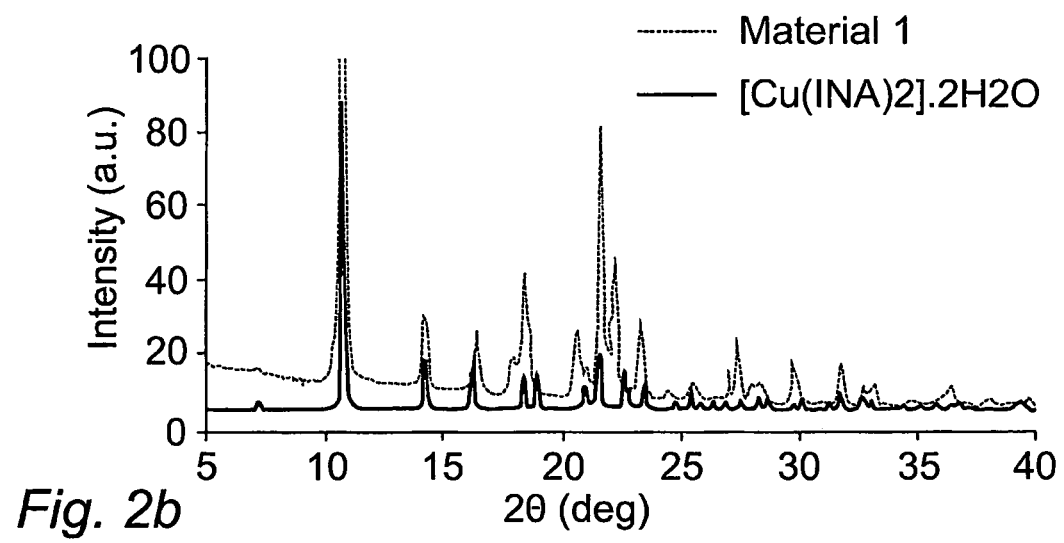
FIG. 2b: Comparison of XRPD pattern of material 1 and the pattern for $[Cu(INA)_2].2H_2O$ calculated from its single-crystal diffraction data.

The X-ray diffraction pattern of material 1 was sufficiently similar to that calculated for the previously known metal-organic framework dihydrate [Cu(INA)$_2$].2H$_2$O (INA=isonicotinate) (FIG. 2b) Single crystal diffraction data for [Cu(INA)$_2$].2H$_2$O were obtained from the Cambridge Structural Database.

During the solvent-free synthesis of this material 1, no evidence of a liquid melt phase was observed even when the grinding was stopped at various intervals to inspect the contents of the reaction vessel. In addition, grinding Cu(OAc)$_2$.H$_2$O and INAH by hand produced an identical colour change to the use of the ball mill, indicating the formation of the same material 1, but once again no liquid phase was observed. These observations make an interesting comparison with certain reactions between organic compounds for which liquid phases have been clearly observed.

Strikingly, it was also found that in the solvent-free synthesis, grinding was actually only required to initiate the reaction, and it was not necessary to continue grinding to drive it to completion. In particular, if grinding was applied for only one minute, the reaction still proceeded in quantative yield to give the final material although the reaction was slower to go to completion, requiring 6 hours overall. The progress of this reaction, as monitored by XRPD. It seems that the essential role for grinding in at least this reaction is to finely divide and intimately mix the two reactants, and that once this has happened the reaction can proceed unaided, although it is accelerated by continued grinding.

Also interesting is that different microscopic morphologies are exhibited by samples prepared by grinding for 1 minute, compared to those prepared for longer times, such as 5 minutes. SEM images taken after two such samples had been left to stand for one week, show that the 1-minute sample consists of crystals which are larger and have more clearly defined faces and edges than those of the 5-minute sample. Clearly, these different morphologies suggest that grinding time during the reaction may part determine the bulk properties of metal-organic frameworks prepared by the solvent-free method of the present invention. The XRPD patterns of a samples prepared by 1 minute of grinding also showed more intense peaks at higher 2-0 values.

Figure 3:
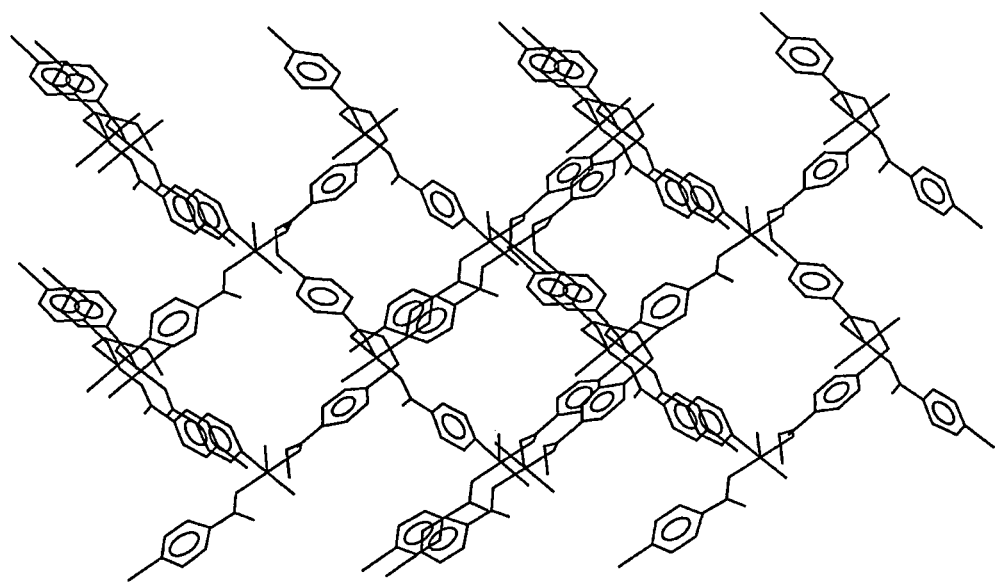
Figure 11:
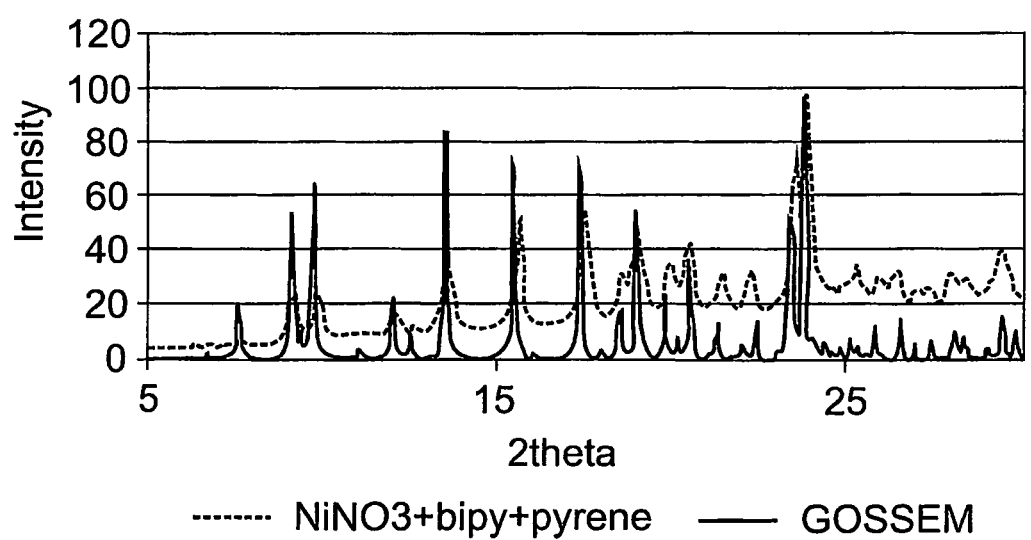
FIG. 11—Comparison of experimental XRPD patterns from the reaction of nickel(II)nitrate, 4,4'-bipyridine and pyrene (top line) with the predicted pattern from the single crystal structure (using the Cambridge Crystallographic Database code GOSSEM) of $[Ni(4,4'-bipyridine)(NO_3)_2].2$pyrene (bottom line).

The compound of Example 1 was previously synthesised "solvothermally" from 4-cyanopyridine, NC$_5$H$_4$-4-CN, and copper chloride, in a mixture of water and ethanol as solvents, by heating the mixture to a temperature of about 150° C. for 48 hours. Its structure consists of isonicotinate ligands linking square-pyramidal Cu(II) centres to form a continuous three-dimensional network, with channels which contain water molecules (FIG. 3). It is closely related to the iron, cobalt and manganese [M(INA)$_2$] structures, but five-coordinate based rather than having octahedral metal centres. The similarity between the XRPD pattern of material 1, and that calculated for [Cu(INA)$_2$].2H$_2$O, indicates that they have sufficiently similar structures. Differences between the two patterns could be due to inclusion of acetic acid in the product material 1, or conformational differences between the frameworks arising from their different methods of synthesis.

After removal from the reaction vessel, samples of material 1 lost between 15-20% by weight on standing in air over several days, due to partial or complete loss of acetic acid and water (as supported by the reduction of the O—H stretching band in IR spectra). After six days, a sample was analysed by TGA, which showed a further 5% weight loss between 25° C. and 150° C. This could be due to loss of remaining acetic acid, or one equivalent of water (loss of water from [Cu(INA)$_2$].H$_2$O corresponds to 4.2% weight loss).

Figure 2C:
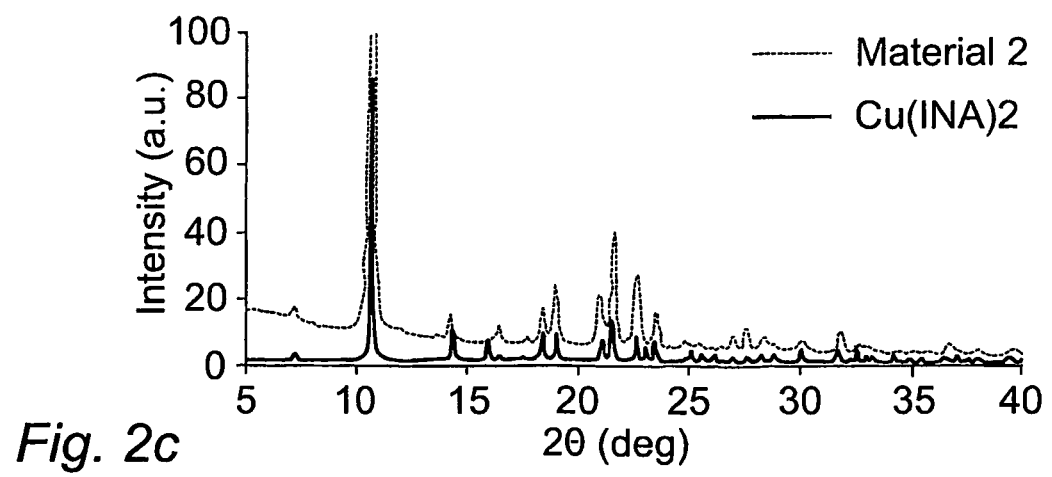
FIG. 2c: Bottom: Comparison of XRPD patterns of material 2 and the calculated pattern for $[Cu(INA)_2]$ FIG. 3—Flat representational X-ray crystal structure of $[Cu(INA)_2]$ as determined by Lu et al. in Chemical Communications 2002, 1340.

Water can be removed from the pores of [Cu(INA)$_2$].2H$_2$O by heating it to 200° C. for three hours, to leave the empty porous host [Cu(INA)$_2$], without disrupting its framework structure. This provides product material 2 (FIG. 1). This material was confirmed to be the empty framework by comparison of its XRPD pattern with that calculated from the known single crystal diffraction data of [Cu(INA)$_2$] (FIG. 2c). In this case, the match between the two patterns is very close.

Analysis calculated for Cu(INA)$_2$.1/2H$_2$O:
C, 45.51; H, 2.84; N, 8.85; Cu, 20.07.
Found for material 2:
C, 45.45; H, 3.07; N, 8.64; Cu, 20.34%

EXAMPLE 2

Synthesis of Cu-BTC

Figure 4:
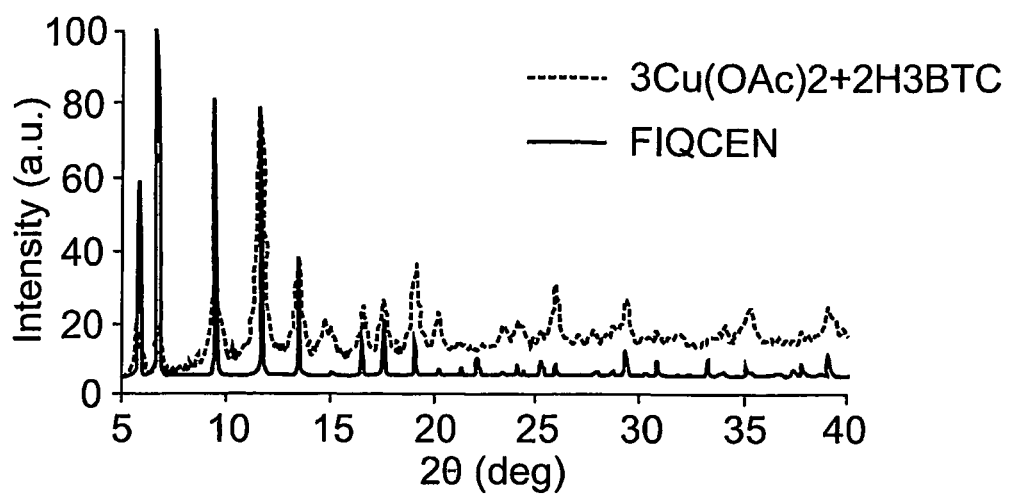
FIG. 4—Comparison of the XRPD pattern of the prepared product and the simulated pattern for $[Cu_3(BTC)_2]$ based on known single-crystal data (Cambridge Crystallographic Database code: FIQCEN).
Figure 5:
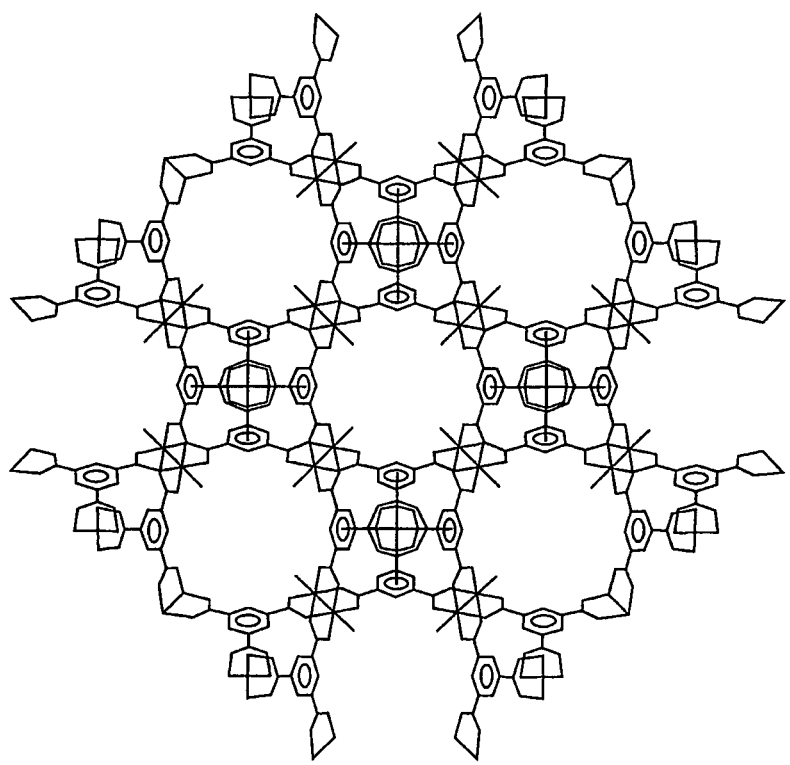
FIG. 5—The porous framework structure of $[Cu_3(BTC)_2].xH_2O$ as previously determined by single-crystal X-ray crystallography. H-atoms and guests in the channels have been omitted for clarity.

The nanoporous framework [Cu$_3$(BTC)$_2$].xH$_2$O was also obtained in quantitative yield after 10 minutes, by reaction between copper acetate and 1,3,5-benzenetricarboxylic acid (H$_3$BTC). The XRPD pattern for the product and the calculated pattern are shown in FIG. 4. The structure as previously determined by single-crystal X-ray crystallography is shown in FIG. 5. It contains wider channels than [Cu(INA)$_2$] at ca. 0.9 nm, with a framework consisting of Cu$_2$(carboxylate) 'paddlewheel' units which are connected into a three dimensional net based on the XX topology. This material has potentially useful gas-separation by a variety of solvent-based methods, ranging from solvothermal conditions over several days, to reflux for several hours.

The mechanochemical method of the present invention clearly presents advantages in terms of time and the avoidance of solvent and external heating. No remaining unreacted ligand or metal salt were observed in the XRPD patterns suggesting a quantitative yield. Thermogravimetric analysis revealed a mass loss of 38.5% on heating up to 300° C. showing that the as-synthesised material contained large amounts of acetic acid and/or water by-products in the channels and/or on its surface. Above 300° C. there was rapid weight loss corresponding to decomposition of the framework. After heating, elemental analysis was consistent with the formula [Cu$_3$(BTC)$_2$].

Similar reactions of three copper salts (acetate, formate and trifluoracetate) with acetylenedicarboxylic acid (H$_2$ADC) also gave crystalline products.
Reactions with Nickel and Zinc Salts.

Figure 6:
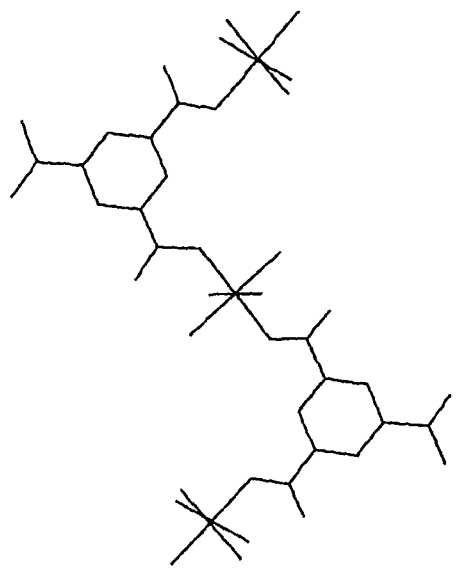
FIG. 6—The discrete trinuclear structure of $[Ni_3(BTC)_2(H_2O))_{14}].4H_2O$ as previously determined by single-crystal X-ray crystallography. H-atoms and water of crystallisation are omitted for clarity.
Figure 9:
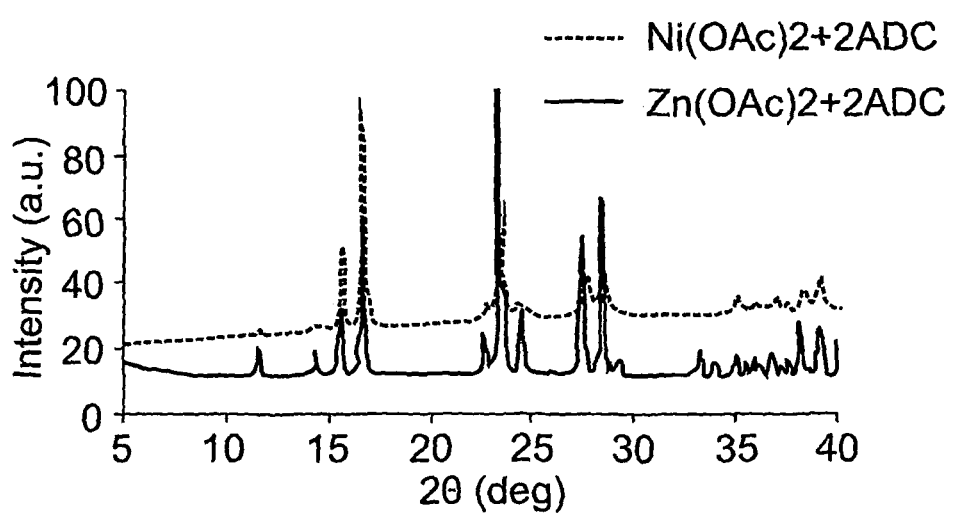
FIG. 9—The comparison of XRPD patterns for reactions between $H_2ADC$ and nickel acetate and zinc acetate.
Figure 7:
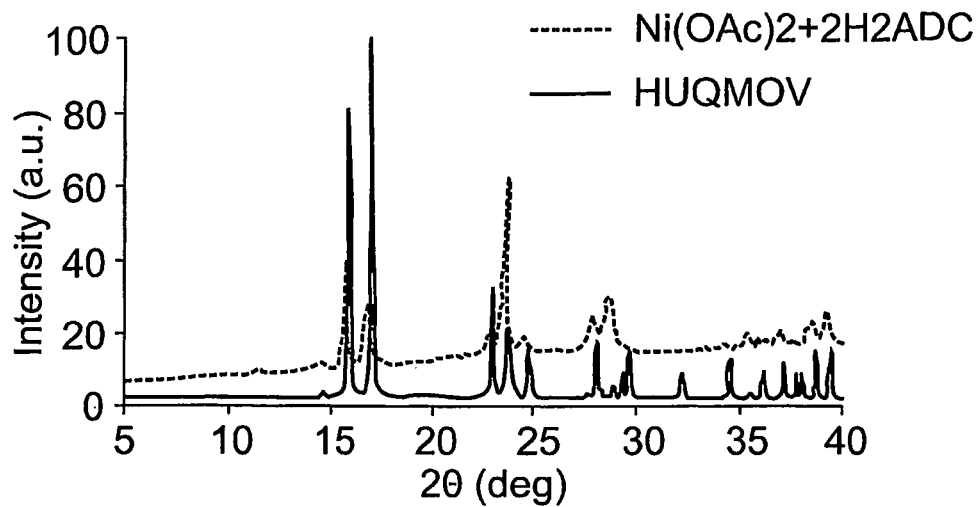
FIG. 7—Comparison of XRPD patterns for the prepared product of the reaction between nickel acetate and $H_2ADC$ with that simulated from the single-crystal data for $[Ni(ADC)(H_2O)_4]$.
Figure 8:
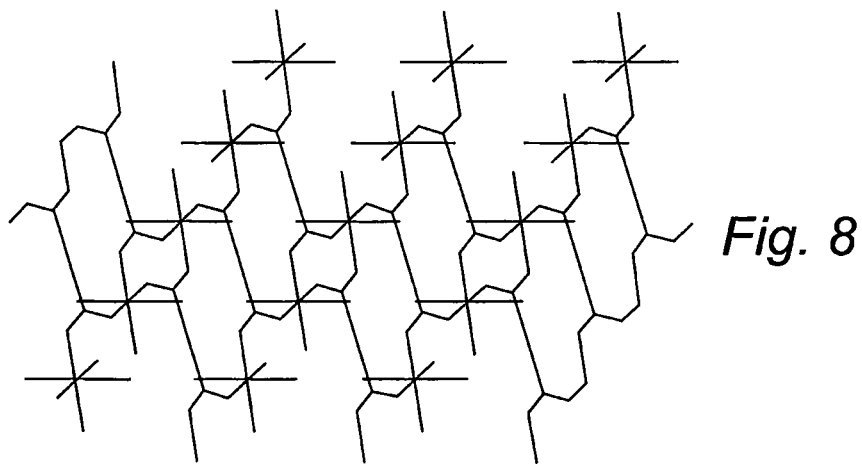
FIG. 8—The three-dimensional framework structure of $[Ni(ADC)(H_2O)_4]$ with H-atoms omitted for clarity.

Reaction of nickel sulfate with H$_3$BTC gave a material whose pattern matched that simulated for [Ni$_3$(BTC)$_2$(H$_2$O)$_{14}$].4H$_2$O. This complex consists of discrete trinuclear species with BTC ligands bridging between octahedral nickel centres, at which aquo ligands take up the remaining coordination sites (FIG. 6). Reaction of H$_2$ADC with nickel acetate gave a crystalline product which still exhibited some peaks due to unreacted ligand. The positions of the new peaks correspond closely to those simulated for the known complex [Ni(ADC)(H$_2$O)$_4$] (FIG. 7). This compound has a 3-dimensional structure as illustrated in FIG. 8. Interestingly, the reaction between zinc acetate and H$_2$ADC gave a remarkably similar pattern, suggesting that the products of the nickel and zinc reactions are isostructural (FIG. 9). The presence of remaining ligand is consistent with the 2:3 (Metal:ligand) stoichiometry used in the reaction, being different to the 1:1 stoichiomerty of the product.

Figure 10:
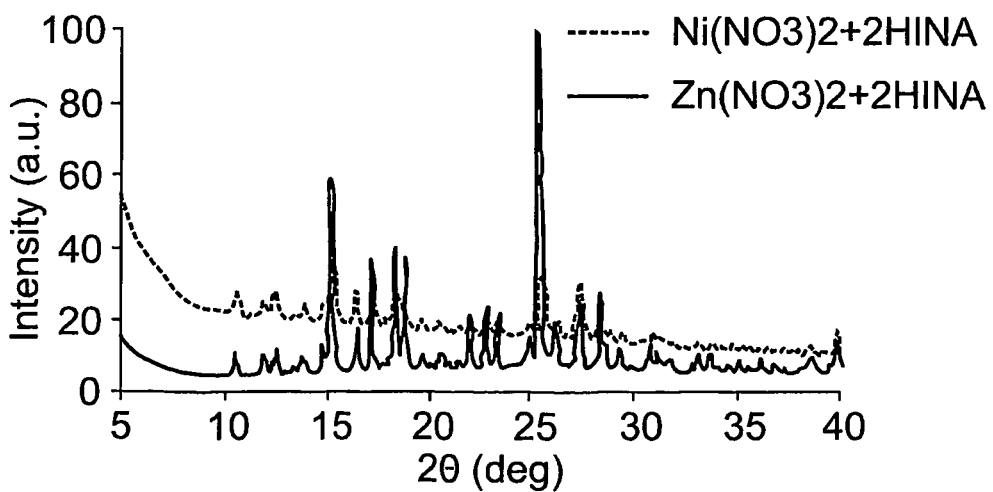
FIG. 10—Comparison of XRPD patterns for the products of reactions between nickel nitrate and HINA, and zinc nitrate and HINA.

Further examples of isostructural nickel and zinc products were obtained from reactions between HINA with nickel nitrate and zinc nitrate (FIG. 10).

The examples of reactivity between metal salts and bridging organic ligands under mechanochemical conditions shows that this method is a very convenient potentially green approach to the preparation of microporous metal-organic frameworks and coordination polymers in general. Quantitative reactions do generally occur under these conditions, to give crystalline products, within minutes, in the absence of solvent. Microporous materials of considerable interest are obtained.

The invention claimed is:

1. A process for the preparation of a multi-dimensional microporous metal-organic compound comprising the steps of:
   providing a first reactant which includes at least one of Cu or Zn in ionic form;
   providing a second reactant which includes a bridging organic ligand comprising at least one bridging atom having at least one non-binding, doublet, wherein the at least one bridging atom is selected from the group consisting of oxygen and nitrogen; and
   grinding the first and second reactants together, wholly or substantially in the absence of solvent.

2. A process as claimed in claim 1 wherein the grinding step is carried out at ambient temperature.

3. A process as claimed in claim 1 wherein the first reactant is a salt, or in salt form.

4. A process as claimed in claim 3 wherein the first reactant is a divalent metal salt $MX_2$ wherein M is Cu, $X_2$ is $(OAc)_2$, $(HCO_3)_2$, $(F_3CCO_2)_2$, $(acac)_2$, $(F_6acac)_2$, $(NO_3)_2$, or $SO_4$; or M is Zn, $X_2$ is $(OAc)_2$, or $(NO_3)_2$.

5. A process as claimed in claim 1 wherein the second reactant is selected from the group consisting of carboxylates, pyridines, amines, carboxylic acids, diacid moieties, and combinations thereof.

6. A process as claimed in claim 1 for the preparation of copper isonicotinate $[Cu(INA)_2]$, wherein the first reactant is copper acetate, and the second reactant is isonicotinic acid.

7. A process as claimed in claim 1 for the preparation of copper benzene-1,3,5-tricarboxylate, wherein the first reactant is copper nitrate, and the second reactant is trimesic acid.

8. A process as claimed in claim 1 wherein the grinding is provided by one or more grinders or grinding means, which grinder or grinding means includes one or more grinding assistants.

9. A process as claimed in claim 8 wherein the grinding assistant comprises one or more grinding balls.

10. A process as claimed in claim 1 wherein the grinding of the first and second reactants is followed by drying.

11. A process as claimed in claim 1, further comprising providing one or more further reactants to provide a multi-metal and/or multi-bridging-substance 2D or 3D microporous metal-organic compound.

12. A process as claimed in claim 11 wherein said one or more further reactant is a second organic ligand.

13. A process as claimed in claim 1 for the preparation of a multi-dimensional microporous metal-organic framework material based on one or more secondary building units.

14. A process according to claim 3 wherein the salt is a nitrate, a sulfate or an acetate.

15. A process according to claim 4 wherein the metal is zinc.

16. A process according to claim 5 wherein the second reactant is selected from the group consisting of 1,4-benzenedicarboxylic acid ($H_2BDC$), acetylenedicarboxylic acid (ADC), 1,3,5-benzenetricarboxylic acid ($H_3BTC$), isonicotinic acid (HINA) and 4,4'-bipyridine.

* * * * *